United States Patent [19]

Silhankova

[11] 4,186,252

[45] Jan. 29, 1980

[54] METHOD FOR PREPARATION OF VITAMIN B1

[75] Inventor: Ludmila Šilhánková, Prague, Czechoslovakia

[73] Assignee: Vysoka skola chemicko-technologicka, Prague, Czechoslovakia

[21] Appl. No.: 792,704

[22] Filed: May 2, 1977

[51] Int. Cl.$^2$ .............................................. C12D 5/02
[52] U.S. Cl. .................................... 435/120; 435/161; 426/11; 426/16; 426/19; 435/940; 435/942

[58] Field of Search ...................... 195/82, 37, 40, 41, 195/DIG. 10

[56] References Cited

U.S. PATENT DOCUMENTS 2,262,735  11/1941  Schulz et al. ........................ 195/82

*Primary Examiner*—Alvin E. Tanenholtz

[57] ABSTRACT

A method for preparing vitamin $B_1$ in a fermentation process involves cultivating mutants of yeast of the genus Saccharomyces Meyen emend Reess that synthesize this vitamin from sugars and inorganic salts and excrete it from living cells into fermentation media.

6 Claims, No Drawings

METHOD FOR PREPARATION OF VITAMIN B1

This invention relates to a process for producing vitamin $B_1$. More particularly, the present invention relates to a process for producing vitamin $B_1$ by fermentation either independently or during the production of ethanol fermented beverages or fermented foodstuffs. Still further, the present invention relates to the production of vitamin $B_1$ by fermentation using special strains of microorganisms that excrete the vitamin from living cells into fermentation media.

It is well-known that in the industrially-developed countries the present state of food technology and the modes of human nutrition, especially the preference for finely-ground white flour and foods preserved by heat treatment lends to a sub-optimum concentration of vitamin $B_1$ in human nourishment and a concurrent increase in the demand for synthetic vitamin $B_1$ for pharmaceutical purposes or, alternatively, a need for the fortification of flour and products thereof.

It is known that in the preparation of most alcoholic beverages, as for example beer, wine, cider, sorghum, sake, quass, etc., yeast strains are employed which deprive the fermenting medium of vitamin $B_1$, the source thereof being raw materials such as malt, cereals, fruits and the like. Unfortunately, the vitamin becomes a part of cells which are removed from the fermenting media after conclusion of the fermentation process. Thus, for example, in the preparation of beer wherein the essential raw material is malt, a material which is rich in vitamin $B_1$, a decrease in vitamin $B_1$ content ranging up to 3 $\mu g$ per liter occurs, such being attributed to the action of brewer's yeast. Much to the dismay of workers in the art, the recovery of vitamin $B_1$ from brewer's yeast is not sufficient to meet the demand for this vitamin for nutritional and pharmaceutical purposes.

Accordingly, to meet such demands, workers in the art have developed techniques for chemically synthesizing the vitamin. However, vitamin $B_1$ has not yet been produced in a one-step fermentation process since microorganisms capable of producing the vitamin on an economical basis from simple carbon sources such as sugars have not been known.

In accordance with the present invention, these prior art limitations are effectively obviated by a novel procedure wherein vitamin $B_1$ is prepared in a fermentation process by means of mutants of yeasts of the genus Saccharomyces Meyen emend Reess that are capable of synthesizing not only vitamin $B_1$ for their own needs, as do other strains of this genus, but also produce the vitamin in excess and excrete considerable amounts thereof into cultivation media.

Accordingly, it is an object of the present invention to prepare vitamin $B_1$ by fermentation in an economic manner as a by-product of industrial alcohol fermentation. It is a further object of the invention to produce vitamin $B_1$ by fermentation during the fermentative preparation of alcoholic beverages such as beer, wine, fruit wines, cider, sorghum, sake, quass, kifir, kumis, etc.

A still further object of the invention is to prepare baker's yeast with characteristics permitting the yeast to produce vitamin $B_1$ in dough during its leavening.

These and other advantages of the present invention will become more apparent to those skilled in the art from a consideration of the following specification and claims.

Thus, in accordance with the present invention, mutated strains of the genus Saccharomyces Meyen emend Reess have been prepared by means of genetic and biochemical methods, such strains being capable of synthesizing vitamin $B_1$ to a high degree even if present in the fermentation medium and also being capable of excreting excess vitamin produced therefrom. These mutated strains are found to be stable in their ability to excrete vitamin $B_1$ and can, therefore, repeatedly be used for the production of vitamin $B_1$ by fermentation. Strains *Saccharomyces cerevisiae* Hansen DBM 159 and *Saccharomyces uvarum* Beijerinck (syn. Sacch. Carlsbergensis Hansen) DBM 189 are particularly suited for this purpose.

Cultivation of the strains employed herein may be effected either in a synthetic culture medium or a natural medium, the prime requirement being that the medium contain the essential nutrients for the growth of the strain employed. Such nutrients are well-known in the art and may typically be selected from among a carbon source, a nitrogen source, inorganic compounds and small amounts of organic growth factors.

Carbon sources found suitable for this purpose include sugars such as glucose, fructose, sucrose, maltose, mallotriose and the like. The source of these sugars may be molasses, malt extract, fruit mash, starch syrup, cellulose hydrolysates, sulfite liquors and the like.

The nitrogen sources employed may be chosen from among various ammonium salts such as ammonium sulfate, ammonium phosphate, liquid ammonia, etc., or natural substances containing nitrogen such as malt extract, yeast extract, casein hydrolysates, cornsteep liquor, etc.

The media employed also include inorganic compounds which must be present to assure growth of the strains employed. Typical of such inorganic compounds are potassium phosphate, magnesium sulfate, iron sulfate, the chlorides of iron or sodium, etc. Traces of other inorganic ions are usually present in sufficient amounts in the raw materials employed to aid in the growth of the strains.

The organic growth factors employed may be biotin, pantothenate, etc. These compositions may be furnished by adding natural substances such as malt extract, yeast extract, cornsteep liquor and the like.

In the operation of the process, the conditions normally employed in culturing and fermentation, are for example, in alcoholic fermentation, baker's yeast production and the production of beer, wines, ciders and the like may be used. Typically, fermentation temperatures range from 6°–10° C. for bottom beer type fermentation and from 30°–32° C. for ethanol production.

Following fermentation, the vitamin may be recovered from the fermentation medium by conventional means such as ion exchange techniques, adsorption, chromatography, gel filtration or the like. A particularly useful ion exchange process is described below in Example 1.

In the preparation of alcoholic beverages fortified with vitamin $B_1$, this end may conveniently be attained by adding the vitamin $B_1$ excreting strains to the innoculum so that the vitamin excreted by the yeast during the fermentation process remains a part of the beverage (and fortifies it). Typical beverages for this purpose include beer, wine, fruit wines, cider, sake, sorghum, quass and lactic fermentation beverages such as kifir, kumis, etc.

Several examples of the present invention as set forth below. It will be understood that these examples are by way of exposition only and are not to be construed as limiting.

EXAMPLE 1

*Saccharomyces cerevisiae* Hansen, strain DBM 159 was propagated from a laboratory culture in a molasses fermentation medium acidified to a pH within the range of 4.2–4.5 and supplemented with ammonium sulfate and ammonium phosphate. Fermentation was effected at temperature of 30°–32° C. After the removal of the yeast, vitamin $B_1$ was obtained from the fermented liquor by passing it through a column of an ion exchanger. The liquor, in this way deprived of the vitamin, was then processed in accordance with conventional distilling techniques. The vitamin, accumulated in an ionex column, was then eluted and isolated from the eluate by precipitation with silver nitrate and decomposition of the precipitate with diluted hydrochloric acid. Vitamin $B_1$ yield was approximately 10 mg per liter of fermented liquor, the ethanol yield being essentially unaffected.

EXAMPLE 2

The propagation of the yeast strain of Example 1 and *Saccharomyces uvarum* Beijerinck DBM 189 was effected in a propagating brewer's station. The preparation of wort and its fermentation were carried out in the manner of bottom brewer's fermentation. After sedimentation of the yeast and skimming of the wort, beer was further processed in conventional brewer's manner. Yeast removed from the primary fermentation process was used in 6 subsequent processes. Beer prepared in the foregoing manner contained vitamin $B_1$ from the raw materials and from the yeast strain *Saccharomyces uvarum* Beijerinck DBM 189, and *Saccharomyces cerevisiae* Hansen DBM 159, respectively.

EXAMPLE 3

5 liters of pasteurized milk supplemented with 100 grams of sucrose was inoculated with the starter used for cultivating *Saccharomyces cerevisiae* DBM 159, above, together with lactic acid bacteria and cocci (such as *Lactobacillus acidophilus, Streptococcus lactis, Streptococcus cremoris*) for 24 hours at 30° C. Following, cooling was effected to a temperature ranging from 10°–15° C. and the fermented milk was ready for distribution and consumption. It contained about 0.8 percent ethanol and an enhanced amount of vitamin $B_1$.

EXAMPLE 4

*Saccharomyces cerevisiae* strain DBM 159 was propagated from a laboratory culture and was used for the production of baker's yeast by means of a conventional aerobic process on a molasses medium supplemented with ammonium phosphate and ammonium sulfate. The baker's yeast so obtained was capable of producing vitamin $B_1$ during the leavening of the dough to which it was added, thereby fortifying the products thereof.

What is claimed is:

1. Method for the preparation of vitamin $B_1$ which comprises fermenting a mutant of yeast which synthesizes and excretes vitamin $B_1$ selected from the group consisting of *Saccharomyces cerevisiae* Hansen DBM 159 and *Saccharomyces uvarum* Beijerinck DBM 189 in a growth medium and recovering the vitamin $B_1$ from the medium.

2. Method in accordance with claim 1, wherein the mutant is *Saccharomyces cerevisiae* Hansen DBM 159.

3. Method in accordance with claim 1, wherein the mutant is *Saccharomyces uvarum* (Carlsbergensis) Beijerinck.

4. Method in accordance with claim 1, wherein the growth medium comprises a source of carbon, a source of nitrogen, a source of phosphorous, trace elements and organic growth factors.

5. Method in accordance with claim 4, wherein the carbon source is molasses, the phosphorous source is ammonium phosphate and the nitrogen source is a mixture of ammonium phosphate and ammonium sulfate.

6. Method in accordance with claim 4, wherein the source of carbon is molasses.

* * * * *